(12) United States Patent
Bigorra Llosas et al.

(10) Patent No.: US 8,461,081 B2
(45) Date of Patent: Jun. 11, 2013

(54) HERBICIDAL COMPOSITIONS CONTAINING GLYPHOSATE

(75) Inventors: Joaquin Bigorra Llosas, Sabadell (ES); Javier Raya, Saint Vicenç dels Horts (ES); Bernd Fabry, Korschenbroich (DE); Rainer Höfer, Düsseldorf (DE); Benoit Abribat, Saint Fargeau Ponthierry (FR)

(73) Assignee: Cognis IP Management GmbH, Duesseldorf (DE)

( * ) Notice: Subject to any disclaimer, the term of this patent is extended or adjusted under 35 U.S.C. 154(b) by 356 days.

(21) Appl. No.: 12/528,126

(22) PCT Filed: Feb. 14, 2008

(86) PCT No.: PCT/EP2008/001115
§ 371 (c)(1),
(2), (4) Date: Aug. 21, 2009

(87) PCT Pub. No.: WO2008/101629
PCT Pub. Date: Aug. 28, 2008

(65) Prior Publication Data
US 2010/0323898 A1    Dec. 23, 2010

(30) Foreign Application Priority Data

Feb. 23, 2007    (EP) .................................... 07003722

(51) Int. Cl.
| | | |
|---|---|---|
| *A01N 37/18* | (2006.01) |
| *A01N 25/00* | (2006.01) |
| *A01N 65/00* | (2009.01) |
| *A61K 9/50* | (2006.01) |
| *A61K 36/00* | (2006.01) |
| *C07C 53/00* | (2006.01) |
| *C07C 57/00* | (2006.01) |
| *C07C 59/00* | (2006.01) |
| *C08G 63/48* | (2006.01) |
| *C11B 1/00* | (2006.01) |

(52) U.S. Cl.
USPC ........... 504/149; 504/334; 504/339; 424/405; 424/502; 424/725; 424/776; 514/383; 514/531; 514/741; 554/1; 554/9

(58) Field of Classification Search
USPC .................. 504/149, 334, 339; 424/405, 502, 424/725, 776; 554/1, 9; 514/383, 531, 741
See application file for complete search history.

(56) References Cited

U.S. PATENT DOCUMENTS

| | | | | |
|---|---|---|---|---|
| 3,342,673 | A | * | 9/1967 | Kaufman et al. ............. 514/443 |
| 3,954,977 | A | | 5/1976 | Rife |
| 5,213,805 | A | * | 5/1993 | Wallach et al. ............... 424/450 |
| 5,489,569 | A | * | 2/1996 | Bryant et al. ................. 504/166 |
| 6,500,783 | B1 | * | 12/2002 | Bryson et al. ................. 504/206 |
| 2001/0019996 | A1 | * | 9/2001 | Soula et al. ................... 504/189 |

FOREIGN PATENT DOCUMENTS

| | | |
|---|---|---|
| EP | 0453899 A1 | 10/1991 |
| EP | 0453899 B1 | 10/1991 |
| WO | 93/01801 | 2/1993 |
| WO | 94/13140 | 6/1994 |
| WO | 95/21525 | 8/1995 |
| WO | 99/02037 | 1/1999 |

OTHER PUBLICATIONS

Table 2, "Fatty acid composition of rapeseed and low erucic acid (canola) oil compared to olive oil, soybean, and sunflower,"; (2007); (downloaded Sep. 30, 2011); ftp://ftp.fao.org/es/esn/food/bio-10t.pdf.*

"Glyphosate", Wikipedia [online] 1994-2001; 2008 [retrieved Apr. 10, 2012]. Retrieved from the Internet: <URL: en.wikipedia.org/wiki/Glyphosate>.*

* cited by examiner

*Primary Examiner* — Jane C Oswecki
(74) *Attorney, Agent, or Firm* — Servilla Whitney LLC

(57) ABSTRACT

The invention relates to biocide compositions, comprising (a) at least one dialkylamide based on oleic and/or linoleic acid, and (b) at least one biocide. The compositions exhibit an improved stability even if stored at temperatures between 5° and 40° C. for an extended period.

8 Claims, No Drawings

HERBICIDAL COMPOSITIONS CONTAINING GLYPHOSATE

CROSS REFERENCE TO RELATED APPLICATIONS

This application is the National Phase entry of PCT/EP2008/001115, filed Feb. 14, 2008 which claims priority to EPO patent application number 07003722 filed Feb. 23, 2007 both of which are incorporated herein by reference in their entireties.

FIELD OF THE INVENTION

The present invention relates to the area of agrochemicals and refers to biocide compositions comprising certain dialkylamides, and to the use of such dialkylamides as solvents or dispersants for biocides.

BACKGROUND OF THE INVENTION

Biocides, and in particular pesticides such as fungicides, insecticides and herbicides, are important auxiliary agents for agriculture in order to protect and to increase the yield of crops. Depending on the various and often very specific needs, a number of actives exist, which show very different chemical structures and behaviours. Nevertheless, it is well known from the state of the art that it remains difficult to prepare aqueous solutions of these actives exhibiting a satisfactory stability, especially if stored over a longer time at very low or elevated temperatures. As a matter of fact, the solutions show a strong tendency to either separate or form crystals, which makes it necessary to re-disperse the actives in the compositions prior to every application in order to obtain a homogenous product. Due to the fact that in spray equipments, which is customarily used for the application of aqueous formulations of plant treatment agents, several filters and nozzles are present, an additional problem appears which is related to the blocking of these filters and nozzles as a result of crystallizing active compound during the application of aqueous spray liquors based on solid active ingredients.

European patent application EP 0453899 B1 (Bayer) discloses the use of dimethylamides derived from saturated $C_6$-$C_{20}$ fatty acids as crystallisation inhibitors for azol derivatives which can be applied as fungicides. Unfortunately, the dimethylamides suggested in the patent are useful for a limited number of actives. Even in case of azols and azol derivatives the ability to inhibit unwanted crystallisation is limited to ambient temperatures, while the products are close to being useless in case the solutions have to be used at temperatures of about 5 to 10° C.

Therefore the problem underlying the present invention has been to avoid the disadvantages of the state of the art and develop new compositions with improved storage stability and reduced tendency to form crystals for a wide range of biocides within a temperature range between 5 and 40° C.

DETAILED DESCRIPTION OF PREFERRED EMBODIMENTS

The present invention refers to biocide compositions, comprising
(a) at least one dialkylamide based on oleic or linoleic acid, and
(b) at least one biocide.

Surprisingly it has been observed that dialkylamides, and preferably dimethylamides obtained from oleic acid or linoleic acid, in particular dimethylamide obtained from colza, soy, sunflower or rape seed acid, show an improved solubilising power compared to dimethylamides from fatty acids as known from the state of the art. Applicant has found that the unsaturated dialkylamides are able to dissolve or disperse a wide range of biocides even under drastic conditions, which means storage times of at least 4 weeks at temperatures between 5 and 40° C. without phase separation or sedimentation.

Dialkylamides

Dialkylamides according to the present invention (component a) can be derived from oleic acid/and or linoleic acid, and more particularly from technical fatty acids rich in said species. Preferably the dialkylamides follow the general formula (I), $$R^1CO-NR^2R^3 \tag{I}$$

in which $R^1CO$ stands for a radical of oleic acid or linoleic acid, and $R^2$ and $R^3$ independently represent hydrogen or alkyl groups having 1 to 4 carbon atoms. The preferred dialkylamides represent dimethylamides. The most preferred species exhibiting the best performance in dissolving or dispersing a wide number of different biocides over a long period and both at low and high temperatures is a mixture of oleic and linoleic acid dimethylamide, preferably in weight ratios of about 10:90 to about 90:10, more preferably about 25:75 to about 75:25, and most preferably about 40:60 to 60:40, as obtained from technical grade colza, rape seed, soy or sunflower fatty acids.

Biocides

A biocide (component b) is a chemical substance capable of killing different forms of living organisms used in fields such as medicine, agriculture, forestry, and mosquito control. Usually, biocides are divided into two sub-groups:

pesticides, which includes fungicides, herbicides, insecticides, algicides, moluscicides, miticides and rodenticides, and antimicrobials, which includes germicides, antibiotics, antibacterials, antivirals, antifungals, antiprotozoals and antiparasites.

Biocides can also be added to other materials (typically liquids) to protect the material from biological infestation and growth. For example, certain types of quaternary ammonium compounds (quats) can be added to pool water or industrial water systems to act as an algicide, protecting the water from infestation and growth of algae.

Pesticides

The U.S. Environmental Protection Agency (EPA) defines a pesticide as "any substance or mixture of substances intended for preventing, destroying, repelling, or mitigating any pest".[1] A pesticide may be a chemical substance or biological agent (such as a virus or bacteria) used against pests including insects, plant pathogens, weeds, mollusks, birds, mammals, fish, nematodes (roundworms) and microbes that compete with humans for food, destroy property, spread disease or are a nuisance. In the following examples, pesticides suitable for the agrochemical compositions according to the present invention are given:

Fungicides

A fungicide is one of three main methods of pest control-chemical control of fungi in this case. Fungicides are chemical compounds used to prevent the spread of fungi in gardens and crops. Fungicides are also used to fight fungal infections. Fungicides can either be contact or systemic. A contact fungicide kills fungi when sprayed on its surface. A systemic fungicide has to be absorbed by the fungus before the fungus dies. Examples for suitable fungicides, according to the present invention, encompass the following species: (3-ethoxypropyl)mercury bromide, 2-methoxyethylmercury chloride, 2-phenylphenol, 8-hydroxyquinoline sulfate, 8-phenylmercurioxyquinoline, acibenzolar, acylamino acid fungicides, acypetacs, aldimorph, aliphatic nitrogen fungicides, allyl alcohol, amide fungicides, ampropylfos, anilazine, anilide fungicides, antibiotic fungicides, aromatic fungicides, aureofungin, azaconazole, azithirami, azoxystrobin, barium polysulfide, to benalaxyl, benalaxyl-M, benodanil, benomyl, benquinox, bentaluron, benthiavalicarb, benzalkonium chloride, benzamacril, benzamide fungicides, benzamorf, benzanilide fungicides, benzimidazole fungicides, benzimidazole precursor fungicides, benzimidazolylcarbamate fungicides, benzohydroxamic acid, benzothiazole fungicides, bethoxazin, binapacryl, biphenyl, bitertanol, bithionol, blasticidin-S, Bordeaux mixture, boscalid, bridged diphenyl fungicides, bromuconazole, bupirimate, Burgundy mixture, buthiobate, butylamine, calcium polysulfide, captafol, captan, carbamate fungicides, carbamorph, carbanilate fungicides, carbendazim, carboxin, carpropamid, carvone, Cheshunt mixture, chinomethionat, chlobenthiazone, chloraniformethan, chloranil, chlorfenazole, chlorodinitronaphthalene, chloroneb, chloropicrin, chlorothalonil, chlorquinox, chlozolinate, ciclopirox, climbazole, clotrimazole, conazole fungicides, conazole fungicides (imidazoles), conazole fungicides (triazoles), copper(II) acetate, copper(II) carbonate, basic, copper fungicides, copper hydroxide, copper naphthenate, copper oleate, copper oxychloride, copper(II) sulfate, copper sulfate, basic, copper zinc chromate, cresol, cufraneb, cuprobam, cuprous oxide, cyazofamid, cyclafuramid, cyclic dithiocarbamate fungicides, cycloheximide, cyflufenamid, cymoxanil, cypendazole, cyproconazole, cyprodinil, dazomet, DBCP, debacarb, decafentin, dehydroacetic acid, dicarboximide fungicides, dichlofluanid, dichlone, dichlorophen, dichlorophenyl, dicarboximide fungicides, dichlozoline, diclobutrazol, diclocymet, diclomezine, dicloran, diethofencarb, diethyl pyrocarbonate, difenoconazole, diflumetorim, dimethirimol, dimethomorph, dimoxystrobin, diniconazole, dinitrophenol fungicides, dinobuton, dinocap, dinocton, dinopenton, dinosulfon, dinoterbon, diphenylamine, dipyrithione, disulfuram, ditalimfos, dithianon, dithiocarbamate fungicides, DNOC, dodemorph, dodicin, dodine, DONATODINE, drazoxolon, edifenphos, epoxiconazole, etaconazole, etem, ethaboxam, ethirimol, ethoxyquin, ethylmercury 2,3-dihydroxypropyl mercaptide, ethylmercury acetate, ethylmercury bromide, ethylmercury chloride, ethylmercury phosphate, etridiazole, famoxadone, fenamidone, fenaminosulf, fenapanil, fenarimol, fenbuconazole, fenfuram, fenhexamid, fenitropan, fenoxanil, fenpiclonil, fenpropidin, fenpropimorph, fentin, ferbam, ferimzone, fluazinam, fludioxonil, flumetover, flumorph, fluopicolide, fluoroimide, fluotrimazole, fluoxastrobin, fluquinconazole, flusilazole, flusulfamide, flutolanil, flutriafol, folpet, formaldehyde, fosetyl, fuberidazole, furalaxyl, furametpyr, furamide fungicides, furanilide fungicides, furcarbanil, furconazole, furconazole-cis, furfural, furmecyclox, furophanate, glyodin, griseofulvin, guazatine, halacrinate, hexachlorobenzene, hexachlorobutadiene, hexachlorophene, hexaconazole, hexylthiofos, hydrargaphen, hymexazol, imazalil, imibenconazole, imidazole fungicides, iminoctadine, inorganic fungicides, inorganic mercury fungicides, iodomethane, ipconazole, iprobenfos, iprodione, iprovalicarb, isoprothiolane, isovaledione, kasugamycin, kresoxim-methyl, lime sulphur, mancopper, mancozeb, maneb, mebenil, mecarbinzid, mepanipyrim, mepronil, mercuric chloride, mercuric oxide, mercurous chloride, mercury fungicides, metalaxyl, metalaxyl-M, metam, metazoxolon, metconazole, methasulfocarb, methfuroxam, methyl bromide, methyl isothiocyanate, methylmercury benzoate, methylmercury dicyandiamide, methylmercury pentachlorophenoxide, metiram, metominostrobin, metrafenone, metsulfovax, milneb, morpholine fungicides, myclobutanil, myclozolin, N-(ethylmercury)-p-toluenesulphonanilide, nabam, natamycin, nitrostyrene, nitrothal-isopropyl, nuarimol, OCH, octhilinone, ofurace, organomercury fungicides, organophosphorus fungicides, organotin fungicides, orysastrobin, oxadixyl, oxathiin fungicides, oxazole fungicides, oxine copper, oxpoconazole, oxycarboxin, pefurazoate, penconazole, pencycuron, pentachlorophenol, penthiopyrad, phenylmercuriurea, phenylmercury acetate, phenylmercury chloride, phenylmercury derivative of pyrocatechol, phenylmercury nitrate, phenylmercury salicylate, phenylsulfamide fungicides, phosdiphen, phthalide, phthalimide fungicides, picoxystrobin, piperalin, polycarbamate, polymeric dithiocarbamate fungicides, polyoxins, polyoxorim, polysulfide fungicides, potassium azide, potassium polysulfide, potassium thiocyanate, probenazole, prochloraz, procymidone, propamocarb, propiconazole, propineb, proquinazid, prothiocarb, prothioconazole, pyracarbolid, pyraclostrobin, pyrazole fungicides, pyrazophos, pyridine fungicides, pyridinitril, pyrifenox, pyrimethanil, pyrimidine fungicides, pyroquilon, pyroxychlor, pyroxyfur, pyrrole fungicides, quinacetol, quinazamid, quinconazole, quinoline fungicides, quinone fungicides, quinoxaline fungicides, quinoxyfen, quintozene, rabenzazole, salicylanilide, silthiofam, simeconazole, sodium azide, sodium orthophenylphenoxide, sodium pentachlorophenoxide, sodium polysulfide, spiroxamine, streptomycin, strobilurin fungicides, sulfonanilide fungicides, sulfur, sultropen, TCMTB, tebuconazole, tecloftalam, tecnazene, tecoram, tetraconazole, thiabendazole, thiadifluor, thiazole fungicides, thicyofen, thifluzamide, thiocarbamate fungicides, thiochlorfenphim, thiomersal, thiophanate, thiophanate-methyl, thiophene fungicides, thioquinox, thiram, tiadinil, tioxymid, tivedo, tolclofos-methyl, tolnaftate, tolylfluanid, tolylmercury acetate, triadimefon, triadimenol, triamiphos, triarimol, triazbutil, triazine fungicides, triazole fungicides, triazoxide, tributyltin oxide, trichlamide, tricyclazole, tridemorph, trifloxystrobin, triflumizole, triforine, triticonazole, unclassified fungicides, undecylenic acid, uniconazole, urea fungicides, validamycin, valinamide fungicides, vinclozolin, zarilamid, zinc naphthenate, zineb, ziram, zoxamide and their mixtures.

Herbicides

An herbicide is a pesticide used to kill unwanted plants. Selective herbicides kill specific targets while leaving the desired crop relatively unharmed. Some of these act by interfering with the growth of the weed and are often based on plant hormones. Herbicides used to clear waste ground are nonselective and kill all plant material with which they come into contact. Herbicides are widely used in agriculture and in landscape turf management. They are applied in total vegetation control (TVC) programs for maintenance of highways and railroads.

Smaller quantities are used in forestry, pasture systems, and management of areas set aside as wildlife habitat. In the following, a number of suitable herbicides are compiled:

2,4-D, a broadleaf herbicide in the phenoxy group used in turf and in no-till field crop production. Now mainly used in a blend with other herbicides that act as synergists, it is the most widely used herbicide in the world, the third most commonly used in the United States. It is an example of synthetic auxin (plant hormone).

Atrazine, a triazine herbicide used in corn and sorghum for control of broadleaf weeds and grasses. It is still used because of its low cost and because it works as a synergist when used with other herbicides, it is a photosystem II inhibitor.

Clopyralid, a broadleaf herbicide in the pyridine group, used mainly in turf, rangeland, and for control of noxious thistles. Notorious for its ability to persist in compost. It is another example of synthetic auxin.

Dicamba, a persistent broadleaf herbicide active in the soil, used on turf and field corn. It is another example of synthetic auxin.

Glyphosate, a systemic nonselective (it kills any type of plant) herbicide used in no-till burndown and for weed control in crops that are genetically modified to resist its effects. It is an example of a EPSPs inhibitor.

Imazapyr, a non-selective herbicide used for the control of a broad range of weeds including terrestrial annual and perennial grasses and broadleaved herbs, woody species, and riparian and emergent aquatic species.

Imazapic, a selective herbicide for both the pre- and post-emergent control of some annual and perennial grasses and some broadleaf weeds. Imazapic kills plants by inhibiting the production of branched chain amino acids (valine, leucine, and isoleucine), which are necessary for protein synthesis and cell growth.

Metolachlor, a pre-emergent herbicide widely used for control of annual grasses in corn and sorghum; it has largely replaced atrazine for these uses.

Paraquat, a nonselective contact herbicide used for no-till burndown and in aerial destruction of marijuana and coca plantings. It is more acutely toxic to people than any other herbicide in widespread commercial use.

Picloram, a pyridine herbicide mainly used to control unwanted trees in pastures and edges of fields. It is another synthetic auxin.

Triclopyr.

Insecticides

An insecticide is a pesticide used against insects in all developmental forms. They include ovicides and larvicides used against the eggs and larvae of insects. Insecticides are used in agriculture, medicine, industry and the household. In the following, suitable insecticides are mentioned:

Chlorinated insecticides such as, for example, Camphechlor, DDT, Hexachlorocyclohexane, gamma-Hexachlorocyclohexane, Methoxychlor, Pentachlorophenol, TDE, Aldrin, Chlordane, Chlordecone, Dieldrin, Endosulfan, Endrin, Heptachlor, Mirex and their mixtures;

Organophosphorus compounds such as, for example, Acephate, Azinphos-methyl, Bensulide, Chlorethoxyfos, Chlorpyrifos, Chlorpyriphos-methyl, Diazinon, Dichlorvos (DDVP), Dicrotophos, Dimethoate, Disulfoton, Ethoprop, Fenamiphos, Fenitrothion, Fenthion, Fosthiazate, Malathion, Methamidophos, Methidathion, Methyl-parathion, Mevinphos, Naled, Omethoate, Oxydemeton-methyl, Parathion, Phorate, Phosalone, Phosmet, Phostebupirim, Pirimiphos-methyl, Profenofos, Terbufos, Tetrachlorvinphos, Tribufos, Trichlorfon and their mixtures;

Carbamates such as, for example, Aldicarb, Carbofuran, Carbaryl, Methomyl, 2-(1-Methylpropyl)phenyl methylcarbamate and their mixtures;

Pyrethroids such as, for example, Allethrin, Bifenthrin, Deltamethrin, Permethrin, Resmethrin, Sumithrin, Tetramethrin, Tralomethrin, Transfluthrin and their mixtures;

Plant toxin derived compounds such as, for example, Derris (rotenone), Pyrethrum, Neem (Azadirachtin), Nicotine, Caffeine and their mixtures.

Rodenticides

Rodenticides are a category of pest control chemicals intended to kill rodents. Rodents are difficult to kill with poisons because their feeding habits reflect their place as scavengers. They would eat a small bit and wait, and if they do not get sick, they would continue eating. An effective rodenticide must be tasteless and odorless in lethal concentrations, and have a delayed effect. In the following, examples for suitable rodenticides are given:

Anticoagulants are defined as chronic (death occurs after 1-2 weeks after ingestion of the lethal dose, rarely sooner), single-dose (second generation) or multiple dose (first generation) cumulative rodenticides. Fatal internal bleeding is caused by a lethal dose of anticoagulants such as brodifacoum, coumatetralyl or warfarin. These substances in effective doses are antivitamins K, blocking the enzymes $K_1$-2,3-epoxide-reductase (this enzyme is preferentially blocked by 4-hydroxycoumarin/4-hydroxythiacoumarin derivatives) and $K_1$-quinone-reductase (this enzyme is preferentially blocked by indandione derivatives), depriving the organism of its source of active vitamin $K_1$. This leads to a disruption of the vitamin K cycle, resulting in an inability of production of essential blood-clotting factors (mainly coagulation factors II (prothrombin), VII (proconvertin), IX (Christmas factor) and X (Stuart factor)). In addition to this specific metabolic disruption, toxic doses of 4-hydroxycoumarin/4-hydroxythiacoumarin and indandione anticoagulants are causing damage to tiny blood vessels (capillaries), increasing their permeability, causing diffuse internal bleedings (haemorrhagias). These effects are gradual; they develop in the course of days and are not accompanied by any nociceptive perceptions such as pain or agony. In the final phase of the intoxication, the exhausted rodent collapses in hypovolemic circulatory shock or severe anemia and dies calmly. Rodenticidal anticoagulants are either first generation agents (4-hydroxycoumarin type: warfarin, coumatetralyl; indandione type: pindone, diphacinone, chlorophacinone), generally requiring higher concentrations (usually between 0.005 and 0.1%), a consecutive intake over days in order to accumulate the lethal dose, they are not very active or inactive after a single feeding and less toxic than second generation agents, which are derivatives of 4-hydroxycoumarin (difenacoum, brodifacoum, bromadiolone and flocoumafen) or 4-hydroxy-1-benzothiin-2-one (4-hydroxy-1-thiacoumarin, sometimes incorrectly referred to as 4-hydroxy-1-thiocoumarin, for reason see heterocyclic compounds), namely difethialone. Second generation agents are far more toxic than first generation agents. They are generally applied in lower concentrations in baits (usually in the order of 0.001-0.005%), and are lethal after single ingestion of bait and are effective also against strains of rodents that have become resistant against first generation anticoagulants; thus the second to generation anticoagulants are sometimes referred to as "superwarfarins". Sometimes anticoagulant rodenticides are potentiated by an antibiotic, most commonly the sulfaquinoxaline. The aim of this association (e.g. warfarin 0.05%+sulfaquinoxaline 0.02%, or difenacoum 0.005%+sulfaquinoxaline 0.02% etc.) is that the antibiotic/bacteriostatic agent suppresses intestinal/gut symbiotic microflora that represents a source of vitamin K. Thus the symbiotic bacteriae are killed, or their metabolism is impaired and the production of vitamin K by them is diminuted, an effect which logically contributes to the action of anticoagulants. Antibiotic agents other than sulfaquinoxaline may be used, for example co-trimoxazole, tetracycline, neomycin or metronidazole. A further synergism used in rodenticidal baits is that of an association of an anticoagulant with a compound with vitamin D-activity, i.e. cholecalciferol or ergocalciferol, (see below). A typical formula used is, e.g., warfarin 0.025-0.05%+cholecalciferol 0.01%. In some countries there are even fixed three-component rodenticides, i.e. anticoagulant+antibiotic+vitamin D, e.g. difenacoum 0.005%+sulfaquinoxaline 0.02%+cholecalciferol 0.01%. Associations of a second-generation anticoagulant with an antibiotic and/or vitamin D are considered to be effective even against the most resistant strains of rodents, though some second generation anticoagulants (namely brodifacoum and difethialone), in bait concentrations of 0.0025-0.005% are so toxic that no known resistant strain of rodents exists, and even rodents resistant against any other derivatives are reliably exterminated by application of these most toxic anticoagulants.

Vitamin $K_1$ has been suggested, and successfully used, as an antidote for pets or humans who and which were either accidentally or intentionally (poison assaults on pets, suicidal attempts) exposed to anticoagulant poisons. In addition, since some of these poisons act by inhibiting liver functions, and in progressed stages of poisoning, several blood-clotting factors as well as the whole volume of circulating blood are missing. A blood transfusion (optionally with the clotting factors present) can save a person's life, who inadvertently took them, which is an advantage over some older poisons.

Metal phosphides have been used as a means of killing rodents and are considered single-dose fast acting rodenticides (death occurs commonly within 1-3 days after single bait ingestion). A dose of bait consisting of food and a phosphide (usually zinc phosphide) is left where the rodents can eat it. The acid in the digestive system of the rodent reacts with the phosphide to generate the toxic phosphine gas. This method of vermin control has possible use in places where rodents are resistant to some of the anticoagulants, particularly for control of house and field mice; zinc phosphide baits are also cheaper than most second-generation anticoagulants, so that sometimes, in cases of large infestation by rodents, their population is initially reduced by copious amounts of zinc phosphide bait applied, and the rest of the population that survived the initial fast-acting poison is then eradicated by prolonged feeding on anticoagulant bait. Inversely, the individual rodents that survived anticoagulant bait poisoning (rest population) can be eradicated by pre-baiting them with nontoxic bait for a week or two (this is important in order to overcome bait shyness and to get rodents used to feeding in specific areas by offering specific food, especially when eradicating rats) and subsequently applying poisoned bait of the same sort as used for pre-baiting until all consumption of the bait ceases (usually within 2-4 days). These methods of alternating rodenticides with different modes of action provides a factual or an almost 100% eradication of the rodent population in the area if the acceptance/palatability of bait is good (i.e., rodents readily feed on it).

Phosphides are rather fast acting rat poisons, resulting in that the rats are dying usually in open areas instead of the affected buildings. Typical examples are aluminum phosphide (fumigant only), calcium phosphide (fumigant only), magnesium phosphide (fumigant only) and zinc phosphide (in baits). Zinc phosphide is typically added to rodent baits in amounts of around 0.75-2%. The baits have a strong, pungent garlic-like odor characteristic for phosphine liberated by hydrolysis. The odor attracts (or, at least, does not repulse) rodents, but it has a repulsive effect on other mammals; birds, however (notably wild turkeys), are not sensitive to the smell. They feed on the bait thus becoming collateral damage.

Hypercalcemia. Calciferols (vitamins D), cholecalciferol (vitamin $D_3$) and ergocalciferol (vitamin $D_2$) are used as rodenticides, which are toxic to rodents for the same reason that they are beneficial to mammals: they are affecting calcium and phosphate homeostasis in the body. Vitamins D are essential in minute quantities (few IUs per kilogram body weight daily, which is only a fraction of a milligram), and like most fat soluble vitamins, they are toxic in larger doses as they readily result in the so-called hypervitaminosis, which is, simply said, poisoning by the vitamin. If the poisoning is severe enough (that is if the dose of the toxicant is high enough), it eventually leads to death. In rodents consuming the rodenticidal bait it causes hypercalcemia by raising the calcium level, mainly by increasing calcium absorption from food, mobilising bone-matrix-fixed calcium into ionised form (mainly monohydrogencarbonate calcium cation, partially bound to plasma proteins, $[CaHCO_3]^+$), which circulates dissolved in the blood plasma, and after ingestion of a lethal dose the free calcium levels are raised sufficiently so that blood vessels, kidneys, the stomach wall and lungs are mineralised/calcificated (formation of calcificates, crystals of calcium salts/complexes in the tissues, thus damaging them), further leading to heart problems (myocard is sensitive to variations of free calcium levels which are affecting both myocardial contractility and excitation propagation between atrias and ventriculas) and bleeding (due to capillary damage), and possibly kidney failure. It is considered to be single-dose, or cumulative (depending on the concentration used; the common 0.075% bait concentration is lethal to most rodents after a single intake of larger portions of the bait), sub-chronic (death occurring usually within days to one week after ingestion of the bait). Applied concentrations are 0.075% cholecalciferol and 0.1% ergocalciferol when used alone. There is an important feature of calciferols toxicology which is that they are synergistic with anticoagulant toxicants. This means that mixtures of anticoagulants and calciferols in the same bait are more toxic than the sum of toxicities of the anticoagulant and the calciferol in the bait, so that a massive hypercalcemic effect can be achieved by a substantially lower calciferol content in the bait and vice-versa. More pronounced anticoagulant/hemorrhagic effects are observed if calciferol is present. This synergism is mostly used in baits low in calciferol because effective concentrations of calciferols are more expensive than effective concentrations of the most anticoagulants. The historically very first application of a calciferol in rodenticidal bait was, in fact, the Sorex product Sorexa® D (with a different formula than today's Sorexa® D) back in the early 1970's, containing warfarin 0.025%+ergocalciferol 0.1%. Today, Sorexa® CD contains a 0.0025% difenacoum+0.075% cholecalciferol combination. Numerous other brand products containing either calciferols 0.075-0.1% (e.g. Quintox®, containing 0.075% cholecalciferol) alone, or a combination of calciferol 0.01-0.075% with an anticoagulant are marketed.

Miticides, Moluscicides and Nematicides

Miticides are pesticides that kill mites. Antibiotic miticides, carbamate miticides, formamidine miticides, mite growth regulators, organochlorine, permethrin and organophosphate miticides all belong to this category.

Molluscicides are pesticides used to control mollusks, such as moths, slugs and snails. These substances include metaldehyde, methiocarb and aluminium sulfate. A nematicide is a type of chemical pesticide used to kill parasitic nematodes (a phylum of worm).

A nematicide is obtained from a neem tree's seed cake; which is the residue of neem seeds after oil extraction. The neem tree is known by several names in the world but was first cultivated in India since ancient times.

Antimicrobials

In the following examples, antimicrobials suitable for agrochemical compositions according to the present invention are given. Bactericidal disinfectants mostly used are those applying active chlorine (i.e., hypochlorites, chloramines, dichloroisocyanurate and trichloroisocyanurate, wet chlorine, chlorine dioxide, etc.), active oxygen (peroxides such as peracetic acid, potassium persulfate, sodium perborate, sodium percarbonate and urea perhydrate), iodine (iodpovidone (povidone-iodine, Betadine), Lugol's solution, iodine tincture, iodinated nonionic surfactants), concentrated alcohols (mainly ethanol, 1-propanol, called also n-propanol and 2-propanol, called isopropanol and mixtures thereof; further, 2-phenoxyethanol and 1- and 2-phenoxypropanols are used), phenolic substances (such as phenol (also called "carbolic acid"), cresols (called "Lysole" in combination with liquid potassium soaps), halogenated (chlorinated, brominated) phenols, such as hexachlorophene, triclosan, trichlorophenol, tribromophenol, pentachlorophenol, Dibromol and salts thereof), cationic surfactants such as some quaternary ammonium cations (such as benzalkonium chloride, cetyl trimethylammonium bromide or chloride, didecyldimethylammonium chloride, cetylpyridinium chloride, benzethonium chloride) and others, non-quarternary compounds such as chlorhexidine, glucoprotamine, octenidine dihydrochloride, etc.), strong oxidizers such as ozone and permanganate solutions;

heavy metals and their salts such as colloidal silver, silver nitrate, mercury chloride, phenylmercury salts, copper sulfate, copper oxide-chloride etc. Heavy metals and their salts are the most toxic and environmentally hazardous bactericides and, therefore, their use is strongly suppressed or forbidden.

Further, also properly concentrated strong acids (phosphoric, nitric, sulfuric, amidosulfuric, toluenesulfonic acids) and alkalis (sodium, potassium, calcium hydroxides), at pH <1 or >13, respectively, particularly below at elevated temperatures (above 60° C.) kill bacteria.

As antiseptics (i.e., germicide agents that can be used on human or animal body, skin, mucoses, wounds and the like), few of the above mentioned disinfectants can be used under proper conditions (mainly concentration, pH, temperature and toxicity toward man/animal). Among them, the following are important:

Some properly diluted chlorine preparations (e.g. Daquin's solution, 0.5% sodium or potassium hypochlorite solution, pH-adjusted to pH 7-8, or 0.5-1% solution of sodium benzenesulfochloramide (chloramine B)), some iodine preparations such as iodopovidone in various galenics (ointment, solutions, wound plasters), in the past also Lugol's solution, peroxides as urea perhydrate solutions and pH-buffered 0.1-0.25% peracetic acid solutions, alcohols with or without antiseptic additives, used mainly for skin antisepsis, weak organic acids such as sorbic acid, benzoic acid, lactic acid and salicylic acid some phenolic compounds such as hexachlorophene, triclosan and Dibromol, and cation-active compounds such as 0.05-0.5% benzalkonium, 0.5-4% chlorhexidine, 0.1-2% octenidine solutions.

Bactericidal antibiotics kill bacteria; bacteriostatic antibiotics only slow down their growth or reproduction. Penicillin is a bactericide, as are cephalosporins. Aminoglycosidic antibiotics can act in both a bactericidal manner (by disrupting cell wall precursor leading to lysis), or bacteriostatic manner (by connecting to 30s ribosomal subunit and reducing translation fidelity leading to inaccurate protein synthesis). Other bactericidal antibiotics according to the present invention include the fluoroquinolones, nitrofurans, vancomycin, monobactams, co-trimoxazole, and metronidazole.

Emulsifiers

In a number of cases it is advantageous to add emulsifiers (component c) to the biocide compositions in order to support the stability of the products. A first preferred group of emulsifiers encompasses non-ionic surfactants such as, for example:

products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;

$C_{12/18}$ fatty acid monoesters and diesters of addition products of 1 to 30 mol ethylene oxide onto glycerol;

glycerol mono- and diesters and sorbitan mono- and diesters of saturated and unsaturated fatty acids containing 6 to 22 carbon atoms and ethylene oxide addition products thereof;

addition products of 15 to 60 mol ethylene oxide onto castor oil and/or hydrogenated castor oil;

polyol ester's and, in particular, polyglycerol esters such as, for example, polyglycerol polyricinoleate, polyglycerol poly-12-hydroxystearate or polyglycerol dimerate isostearate. Mixtures of compounds from several of these classes are also suitable;

addition products of 2 to 15 mol ethylene oxide onto castor oil and/or hydrogenated castor oil;

partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

mono-, di and trialkyl phosphates and mono-, di- and/or tri-PEG-alkyl phosphates and salts thereof;

wool wax alcohols;

polysiloxane/polyalkyl polyether copolymers and corresponding derivatives;

mixed esters of pentaerythritol, fatty acids, citric acid and fatty alcohol and/or mixed esters of $C_{6-22}$ fatty acids, methyl glucose and polyols, preferably glycerol or polyglycerol, polyalkylene glycols and glycerol carbonate.

The addition products of ethylene oxide and/or propylene oxide onto fatty alcohols, fatty acids, alkylphenols, glycerol mono- and diesters and sorbitan mono- and diesters of fatty acids to or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

Partial Glycerides

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30, and preferably 5 to 10, mol ethylene oxide onto the partial glycerides mentioned are also suitable.

Sorbitan Esters

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan tri hydroxystearate, sorbitan monotartrate, sorbitan sesquitartrate, sorbitan ditartrate, sorbitan tri tartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30, and preferably 5 to 10, mol ethylene oxide onto the sorbitan esters mentioned are also suitable.

Polyglycerol Esters

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyesters are the mono-, di- and triesters of trimethylol propane or pentaerythritol with lauric acid, cocofatty acid, tallow fatty acid, palmitic acid, stearic acid, oleic acid, behenic acid and the like, optionally reacted with 1 to 30 mol ethylene oxide.

Typical anionic emulsifiers are aliphatic $C_{12-22}$ fatty acids such as palmitic acid, stearic acid or behenic acid, for example, and $C_{12-22}$ dicarboxylic acids such as azelaic acid or sebacic acid, for example.

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —$SO_3H$— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkyl-aminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Biocide Compositions

Typically, the compositions according to the present invention comprise (a) about 0.1% b.w. to about 99% b.w., preferably about 5% b.w. to about 90% b.w., and most preferably about 15% b.w. to about 25% b.w., dialkylamides derived from oleic acid and/or linoleic acid,
(b) about 1% b.w. to about 99.1% b.w., preferably about 2% b.w. to about 80% b.w., and most preferably about 5% b.w. to about 15% b.w., biocides, and
(c) 0 b.w. to about 10% b.w., and preferably 1 to 5% b.w., emulsifiers on condition that the amounts add with water to 100% b.w. Usually, the active matter content (which means the sum of components a+b+c) is about 5% b.w. to about 50% b.w., and preferably about 10% b.w. to about 25% b.w., calculated on the total of the aqueous composition.

INDUSTRIAL APPLICATION

A final embodiment of the present invention is related to the use of dialkylamides based on oleic acid and/or linoleic acid, in particular dimethylamides based on technical grade colza, rape seed, soy or sunflower acid as solvents or dispersants for biocides.

EXAMPLES

Examples 1 to 6, Comparative Examples C1 and C2

Several aqueous concentrates were prepared by mixing biocides, dimethylamides and emulsifiers in water until a homogeneous solution was obtained. The concentrates were subsequently diluted with water in order to achieve an active matter concentration of 10% b.w. The products thus obtained were stored over a period of 10 to 40 days at temperatures of 5, 20 and 40° C. The stability of the mixtures was observed by inspection and determined according to the following scale: (++)=stable; (+)=slight phase separation/formation of some crystals; (o)=significant phase separation/sedimentation; (−) phases clearly separated/strong sedimentation of crystals. The results are compiled in Table 1. The amounts reflect the composition of the concentrates.

TABLE 1

Stability of biocide compositions

| | 1 | 2 | 3 | 4 | 5 | 6 | C1 | C2 |
|---|---|---|---|---|---|---|---|---|
| Composition [% b.w.] | | | | | | | | |
| Biphenyl | 35 | — | — | — | — | — | — | — |
| Glyphosphate | — | — | — | — | 25 | — | 35 | — |
| Deltametrin | — | — | 35 | — | — | 25 | — | 35 |
| Glucoprotamin | — | — | — | 35 | — | — | — | — |
| Lactic acid dimethylamide | 25 | 25 | 25 | 25 | 15 | 15 | — | — |
| Stearic acid dimethylamide | — | — | — | — | — | — | 25 | 25 |
| Sorbitanmono/dilaurate + 20EO | 10 | 10 | 5 | 5 | — | — | — | — |
| Polyglyceryl-2 Dipolyhydroxystearate | — | — | 5 | 5 | 10 | 10 | — | — |
| Water | | | | add to 100 | | | | |
| Stability | | | | | | | | |
| after 10 days, 5° C. | ++ | ++ | ++ | ++ | ++ | ++ | o | o |
| after 20 days, 5° C. | + | + | ++ | ++ | ++ | ++ | − | − |
| after 40 days, 5° C. | o | o | + | + | + | ++ | − | − |
| after 10 days, 20° C. | ++ | ++ | ++ | ++ | ++ | ++ | ++ | ++ |
| after 20 days, 20° C. | ++ | ++ | ++ | ++ | ++ | ++ | ++ | ++ |
| after 40 days, 20° C. | ++ | ++ | ++ | ++ | ++ | ++ | + | + |
| after 10 days, 40° C. | ++ | ++ | ++ | ++ | ++ | ++ | + | + |
| after 20 days, 40° C. | ++ | ++ | ++ | ++ | ++ | ++ | o | o |
| after 40 days, 40° C. | + | + | + | + | ++ | ++ | o | o |

What is claimed is:

1. A herbicide composition with improved storage stability and reduced tendency to form crystals, comprising:
    (a) at least one oleic acid and/or linoleic acid dialkylamide, and
    (b) at least one glyphosate
    wherein the dialkylamide and the glyphosate are present in a ratio effective to inhibit phase separation or sedimentation when stored for at least 4 weeks at temperatures between 5 and 40° C.

2. The composition of claim 1 wherein component (a) comprises at least one dialkylamide of formula (I), $$R^1CO-NR^2R^3 \qquad (I)$$

in which $R^1CO$ represents an oleic and/or linoleic acid moiety, and $R^2$ and $R^3$ independently represent alkyl groups having 1 to 4 carbon atoms.

3. The composition of claim 1 wherein component (a) comprises at least one dialkylamide based on technical grade fatty acids selected from the group consisting of colza, rape seed, soy and sunflower fatty acids.

4. The composition of claim 1 wherein component (a) is a mixture of oleic acid dimethylamide and linoleic acid dimethylamide in a weight ratio of 10:90 to 90:10.

5. The composition of claim 1 further comprising as component (c) at least one emulsifier.

6. A herbicide composition comprising:
    (a) 0.1% to 99% by weight, based on the composition, of at least one oleic acid and/or linoleic acid dialkylamide,
    (b) 1% to 99.1% by weight, based on the composition, of at least one glyphosate, and
    (c) 0% to 10% by weight, based on the composition, of at least one emulsifier provided that the amounts, including water, total 100%, and wherein the dialkylamide dissolves or disperses the glyphosate when stored for at least 4 weeks at temperatures between 5 and 40° C. without phase separation or sedimentation.

7. The composition of claim 6 wherein the sum of components (a)+(b)+(c) equals 5% to 50% by weight, based on the composition.

8. A method of dissolving or dispersing a glyphosate herbicide comprising adding at least one oleic acid and/or linoleic acid dialkylamide to aid in dissolving or dispersing at least one glyphosate wherein the dialkylamide and the glyphosate are present in a ratio effective to inhibit phase separation or sedimentation when stored for at least 4 weeks at temperatures between 5 and 40° C.

* * * * *